US00PP20714P2

(12) United States Plant Patent
Hofmann

(10) Patent No.: US PP20,714 P2
(45) Date of Patent: Feb. 2, 2010

(54) *MANDEVILLA* PLANT NAMED 'FISRIX DERED'

(50) Latin Name: ***Mandevilla sanderi* (Hemsl.) Woodson**
Varietal Denomination: Fisrix Dered

(75) Inventor: Birgit Christa Hofmann, Rüdesheim (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/220,223

(22) Filed: Jul. 23, 2008

(51) Int. Cl.
*A01H 5/00* (2006.01)

(52) U.S. Cl. ..... Plt./232
(58) Field of Classification Search ..... Plt./232
See application file for complete search history.

(56) References Cited

U.S. PATENT DOCUMENTS

PP15,539 P2 * 2/2005 Misato et al. ..... Plt./232

* cited by examiner

*Primary Examiner*—Susan B McCormick Ewoldt
(74) *Attorney, Agent, or Firm*—S. Matthew Edwards

(57) ABSTRACT

A new *Mandevilla* plant named 'Fisrix Dered,' particularly distinguished by deep red, medium sized flowers, floriferous habit, medium green, glossy leaves, very good branching ability and moderately vigorous, medium to tall, bushy plant habit.

2 Drawing Sheets

Latin name of the genus and species of the plant claimed: *Mandevilla sanderi* (Hemsl.) Woodson.

Varietal denomination: 'Fisrix Dered'.

BACKGROUND OF THE NEW PLANT

The present invention comprises a new and distinct cultivar of *Mandevilla,* botanically known as *Mandevilla sanderi,* and hereinafter referred to by the variety name 'Fisrix Dered.'

'Fisrix Dered' is a product of a planned breeding program. The new cultivar 'Fisrix Dered' has deep red colored flowers, is early flowering and floriferous, and has very good branching characteristics.

'Fisrix Dered' originated from a hybridization made in the summer of 2003 in Hillscheid, Germany. The female parent is the commercial *Mandevilla* variety offered as 'Sundaville'® Red, 'Moulin Rouge' in France, which is identical to 'Sunmandecrim,' U.S. Plant Pat. No. 15,539, having red flower color, good branching characteristics, and medium green to grass green foliage. The male parent is the commercial *Mandevilla* variety offered as'My Fair Lady'™ and patented as 'Helle,' U.S. Plant Pat. No. 9,117, with white to pale pink flower color, deep green foliage, and relatively few branches.

The seeds produced by the hybridization were sown in the fall of 2003. The resulting seedlings (plants) were evaluated in late summer to fall of 2004. 'Fisrix Dered' was selected as one flowering plant in a greenhouse in Hillscheid, Germany.

The plant has been asexually reproduced for the first time in the fall of 2004 and it has been propagated repeatedly by vegetative cuttings in Hillscheid, Germany over a 2–3 year period. Horticultural examination of plants grown from cuttings of the plant initiated in Hillscheid, Germany, in the spring of 2005, and continuing thereafter, has demonstrated that the combination of characteristics as herein disclosed for 'Fisrix Dered' are firmly fixed and are retained through successive generations of asexual reproduction.

Plant Breeder's Rights for this cultivar were applied for in European on Dec. 13, 2006 and in Canada on Jan. 28, 2008.

'Fisrix Dered' has not been made publicly available more than one year prior to the filing of this application.

DESCRIPTION OF THE PHOTOGRAPH

This new *Mandevilla* plant is illustrated by the accompanying photographs which show blooms, buds, and foliage of the plant in full color. The colors shown are as true as can be reasonably obtained by conventional photographic procedures.

The photograph is of a 10 month old plant grown in a greenhouse from the late summer of 2006 to early summer of 2007.

The second photograph shows a flower and a bud.

DETAILED BOTANICAL DESCRIPTION

The following detailed descriptions set forth the distinctive characteristics of 'Fisrix Dered.' The data which define these characteristics were collected from asexual reproductions carried out in Hillscheid, Germany. The plant history was taken in early June 2007 on 9 month old plants grown in 12 cm diameter pots in a glass-covered greenhouse.

Color readings were taken under natural light. Color references are primarily to The R.H.S. Colour Chart of The Royal Horticultural Society of London (R.H.S.) (2001 edition). Texture description details were observed under a magnifying glass.

BRIEF SUMMARY OF INVENTION

The following are the most outstanding and distinguishing characteristics of this new cultivar when grown under normal horticultural practices in Hillscheid, Germany.

1. Deep red colored, medium sized flowers
2. Floriferous, and inflorescences with relatively many flowers
3. Medium green, glossy foliage, ovate leaves 4. Moderately vigorous growth with very good branching characteristics
5. Relatively upright, medium to tall plant habit

COMPARISON WITH PARENTAL AND COMMERCIAL CULTIVARS

'Fisrix Dered' differs from the female parent, *Mandevilla* plant 'Sunmandecrim' U.S. Plant Pat. No. 15,539, in that 'Fisrix Dered' has a somewhat deeper red overall flower color, and especially a deeper and more uniformly red of the flower funnel, while 'Sunmandecrim' shows cherry to pink funnel color. Additionally, 'Fisrix Dered' has a more upright plant habit, and somewhat wider leaves.

'Fisrix Dered' differs from the male parent, the commercial *Mandevilla* plant 'Helle' U.S. Plant Pat. No. 9,117, in that 'Fisrix Dered' has a different flower color (red in contrast to pale pink to white) and is more freely branching.

'Fisrix Dered' differs from the commercial cultivar 'Red Riding Hood' (unpatented) in that 'Fisrix Dered' has a deeper red overall flower color, somewhat less green foliage and develops a higher number of branches.

DESCRIPTION OF THE PLANT

Classification:
- *Family.*—Apocynaceae.
- *Botanical name.*—*Mandevilla sanderi* (Hemsl.) Woodson.

Parentage:
- *Female parent.*—'Sunmandecrim,' a red flowered commercial *Mandevilla* variety (U.S. Plant Pat. No. 15,539).
- *Male parent.*—'Helle,' a commercial, pale pink flowered *Mandevilla* plant (U.S. Plant Pat. No. 9,117).

Whole plant:
- *Form and growth habit.*—Perennial or sub-shrub with herbaceous younger stems and vines, and woody bases, initially upright, develops vines mainly during winter months at low light conditions; commercially mostly grown as an annual plant.
- *Height.*—35–45 cm (from top of soil) on average for 9 month old plants.
- *Width.*—32–40 cm for the foliage (without flowers), respective 45 cm for plant diameter including inflorescences.
- *Time to produce a finished flowering plant.*—About 5 months for a 12 cm pot.
- *Outdoor plant performance.*—Plant in full sun, is free flowering through the summer, has good heat and drought tolerance.
- *Time to initiate and develop roots.*—About 25 days.
- *Root description.*—Fibrous, somewhat fleshy, and freely branching.

Stems:
- *Number of (main) branches.*—11–13.
- *Length.*—Mainly from 25–42 cm.
- *Diameter.*—0.4 cm as measured in the middle.
- *Internode length.*—2.5–4.5 cm.
- *Color.*—Upper two thirds: Light green, RHS 143C; near base: RHS 146C, resp. RHS 177D woody base.
- *Texture.*—Upper parts herbaceous and glabrous; smooth to mucronate; near the base woody, with the surface a little rugose.

Leaves:
- *Arrangement.*—Opposite, mostly decussate.
- *Shape.*—Elliptical to ovate.
- *Apex.*—Acuminate.
- *Base.*—Mostly rounded, occasionally truncate or subcordate.
- *Margin.*—Entire.
- *Immature.*—Color: Upper surface: RHS 143B. Lower surface: RHS 143D.
- *Mature (full expanded).*—Length: 7.0–8.5 cm. Width: 4.5–5.2 cm. Color: Upper surface: RHS 137A to 137C. Lower surface: RHS 138B.
- *Venation.*—Type: Pinnate. Color: RHS 144A, lower side RHS 145B. Texture: Leathery, glossy, glabrous, smooth apart from the slightly protruding midrib on lower side.
- *Petiole.*—Length: 0.9–1.2 cm. Width: 2 or 2.5 mm. Color: RHS 145A upper side, RHS 145B lower side.

Flower bud (just before unfolding the petals):
- *Shape.*—Spindle shaped.
- *Diameter.*—1.3 cm.
- *Length.*—Approximately 6.8–7.5 cm.
- *Color (at tight bud).*—Deep red, RHS 53A at the tips to 53B middle portion: base light Green, RHS 145B to 145C.

Inflorescence:
- *Inflorescence type.*—Raceme emerging from the nodes of the stems with the flowers in an alternative arrangement.
- *Blooming habit.*—Continuously through the summer months.
- *Quantity of inflorescences per plant.*—10–14.
- *Quantity of flowers per inflorescence.*—5–6, in various stages of development.
- *Lastingness of individual blooms on the plant.*—Approximately 10 days.
- *Fragrance.*—None.
- *Inflorescence length.*—11–14 cm.
- *Peduncle.*—Color: RHS 143C, light green. Length: Most often 4–7 cm. Diameter: About 2–3 mm. Texture: Smooth, glabrous.

Flower:
- *Type.*—Single.
- *Shape of corolla.*—Lower part of corolla is tube to funnel shaped former by the fused lower parts of the 5 petals; upper part remains somewhat funnel shaped, with the free petal lobes slanting outwards.
- *Diameter ('face').*—7.5–8.0 cm.
- *Length (depth).*—6–6.5 cm.
- *Diameter of flower throat at opening.*—1.7–1.8 cm.
- *Color upper surface ('face' color).*—Young nearly as dark as RHS 46A, at medium stage mainly RHS 46B with deeper shades.
- *Color corolla underside.*—Near RHS 53A.
- *Color funnel inside surface.*—Orange, RHS 34B.
- *Color funnel, outside.*—Red, intensity decreasing towards base, RHS 53B to 53C.

Petals:
- *Arrangement.*—Lower parts fused, free upper lobes opening outwards and slightly overlapping.
- *Shape of free lobes.*—Roughly ovate to triangular, asymmetric, with the right part wider than the left one.
- *Apex.*—Acute to acuminate.
- *Base.*—Fused.
- *Margin.*—Entire, somewhat wavy.

*Texture.*—Smooth.
*Length* (*from the corolla opening*).—3.9–4.2 cm.
*Width, maximum.*—3.1–3.3 cm.

Calyx: 5 sepals, small, surrounding and closely attached to the base of the flower.
*Color.*—Light green, RHS 154A to 145B, the tiny tips are reddish pink, approximately RHS 54A; margins semi-transparent.
*Length.*—0.9–1.0 cm.
*Width.*—0.2 cm.
*Shape.*—Ligulate.
*Apex.*—Acute, almost spine-like, though soft.
*Base.*—Fused.
*Texture.*—Glabrous.

Pedicels:
*Color.*—Light green, RHS 143C.
*Length.*—About 1.5–1.7 cm.
*Diameter.*—2–3 mm.
*Texture.*—Glabrous.

Reproductive organs:
Stamens: Quantity: 5, connivent, surrounding the style and stigma. Filaments: Fused with the base of the flower. Anther color: Light orange, RHS 20D. Pollen amount: Moderate. Pollen color: RHS 11D.
*Pistils.*—Quantity: 1. Length: 2.5 cm. Stigma color: RHS 154D, pale yellowish green, 5-lobed. Style color: RHS 150D, cream.

Fruit and seed set: Spontaneous seed set has not been observed to date.

Disease/pest resistance: No special tolerance or resistance has been observed to date.

What is claimed is:

1. A new and distinct variety of *Mandevilla* plant named 'Fisrix Dered,' substantially as illustrated and described herein.

* * * * *

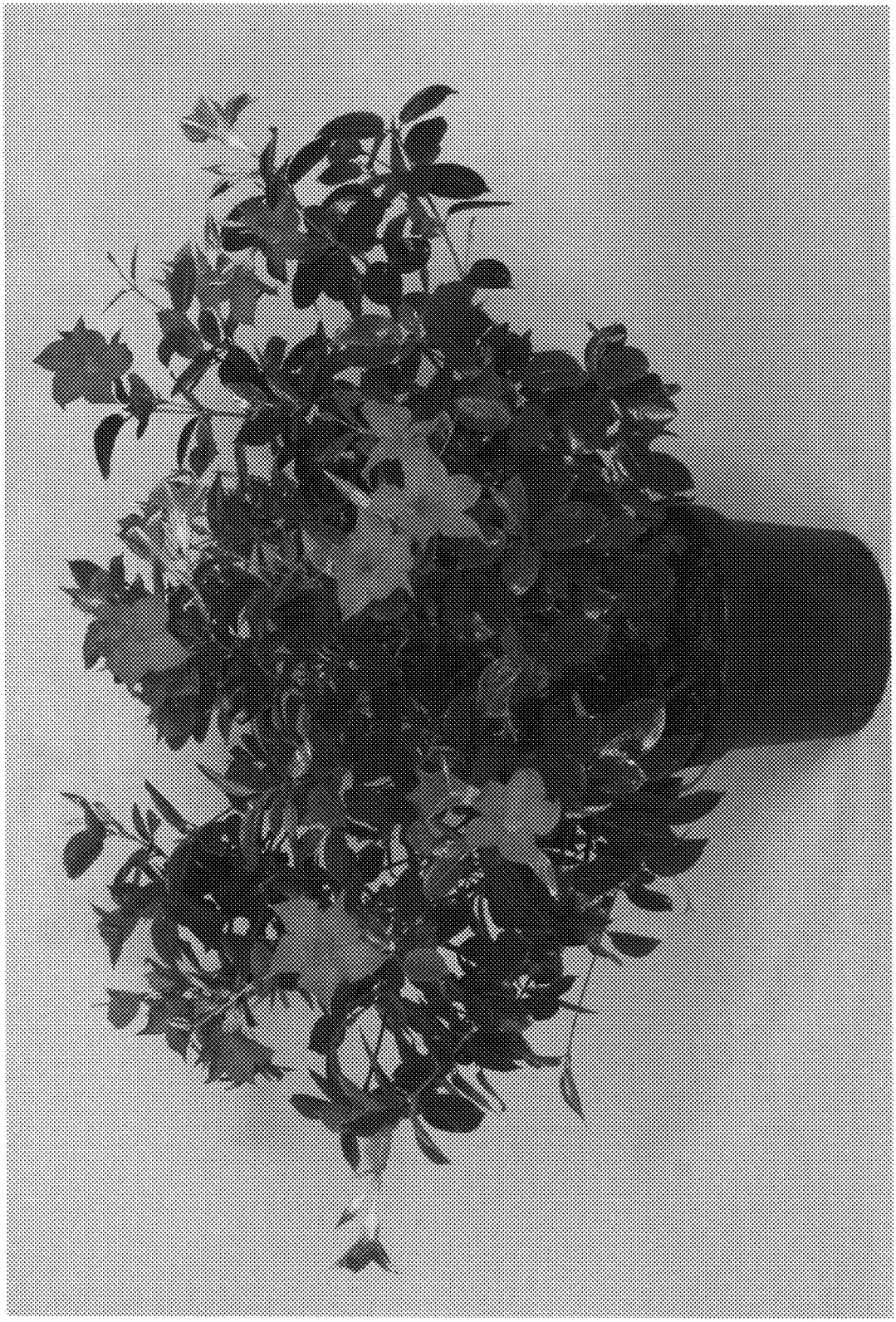

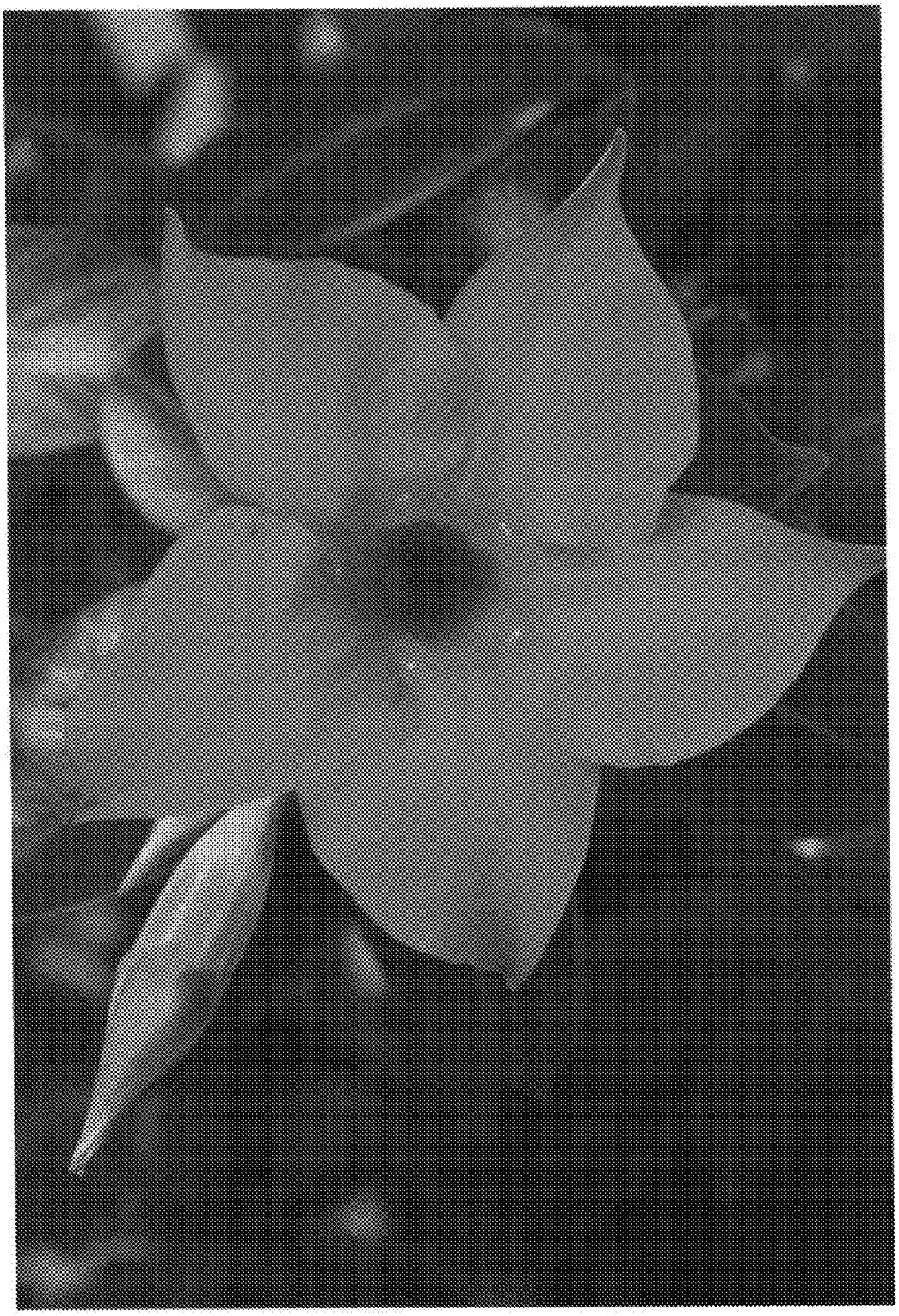

UNITED STATES PATENT AND TRADEMARK OFFICE

CERTIFICATE OF CORRECTION

PATENT NO. : PP 20,714 P2
APPLICATION NO. : 12/220223
DATED : February 2, 2010
INVENTOR(S) : Hofmann It is certified that error appears in the above-identified patent and that said Letters Patent is hereby corrected as shown below:

At column 1, line 38, delete "European" and insert therefor --Europe--

At column 4, line 45, delete "former" and insert therefor --formed--

Signed and Sealed this

Sixth Day of April, 2010

David J. Kappos

David J. Kappos
*Director of the United States Patent and Trademark Office*